(12) United States Patent
Shariff et al.

(10) Patent No.: US 9,045,352 B2
(45) Date of Patent: Jun. 2, 2015

(54) TOTAL FLUID MANAGEMENT SYSTEM

(75) Inventors: Ruzbeh N. Shariff, Santa Clara, CA (US); James Lescoulie, Irvine, CA (US); Reid S. Cover, Mountain View, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 962 days.

(21) Appl. No.: 13/135,662

(22) Filed: Jul. 12, 2011

(65) Prior Publication Data

US 2012/0043269 A1  Feb. 23, 2012

Related U.S. Application Data

(60) Provisional application No. 61/401,884, filed on Aug. 20, 2010.

(51) Int. Cl.
| | | |
|---|---|---|
| B01F 15/02 | (2006.01) | |
| C02F 9/00 | (2006.01) | |
| C02F 1/00 | (2006.01) | |
| A61M 1/34 | (2006.01) | |
| B01F 3/08 | (2006.01) | |
| C02F 1/32 | (2006.01) | |
| C02F 1/44 | (2006.01) | |
| C02F 1/68 | (2006.01) | |
| C02F 103/04 | (2006.01) | |

(52) U.S. Cl.
CPC .................. *C02F 9/00* (2013.01); *B01F 3/0803* (2013.01); *B01F 15/0203* (2013.01); *C02F 1/00* (2013.01); *C02F 1/32* (2013.01); *C02F 1/441* (2013.01); *C02F 1/444* (2013.01); *C02F 1/68* (2013.01); *C02F 2103/04* (2013.01); *C02F 2303/04* (2013.01); *A61M 1/3462* (2013.01)

(58) Field of Classification Search
CPC . B01F 3/0803; B01F 15/00831; A61M 34/62
USPC ........................................................ 366/152.4
See application file for complete search history.

(56) References Cited

U.S. PATENT DOCUMENTS

| | | |
|---|---|---|
| 3,616,921 A | 11/1971 | Bray |
| 3,774,763 A | 11/1973 | Yall et al. |
| 4,072,610 A | 2/1978 | Gow et al. |
| 4,280,912 A | 7/1981 | Berry, III et al. |
| 4,495,067 A | 1/1985 | Klein et al. |
| 4,587,518 A | 5/1986 | King |
| 4,600,512 A | 7/1986 | Aid |
| 4,773,991 A | 9/1988 | Aid |
| 4,784,495 A | 11/1988 | Jonsson et al. |
| 4,857,184 A | 8/1989 | DeLoach |
| 5,032,265 A | 7/1991 | Jha et al. |
| 5,167,808 A | 12/1992 | Carr et al. |

(Continued)

FOREIGN PATENT DOCUMENTS

WO  WO 92/03202  3/1992

*Primary Examiner* — Tony G Soohoo
(74) *Attorney, Agent, or Firm* — Flynn, Thiel, Boutell & Tanis, P.C.

(57) ABSTRACT

A system for the management of fluid, such as saline solution for medical procedures, is provided. The system generally includes a water purification station and a portable fluid station, which is dockable to the water purification station. The portable fluid station is capable of combining purified water from the water purification station with a concentrate in powder or liquid form to create a usable solution. A method of using such a system is also provided.

13 Claims, 3 Drawing Sheets

(56) References Cited

U.S. PATENT DOCUMENTS

| | | |
|---|---|---|
| 5,167,816 A | 12/1992 | Kruger et al. |
| 5,259,954 A | 11/1993 | Taylor |
| 5,312,547 A | 5/1994 | Kruger et al. |
| 5,352,364 A | 10/1994 | Kruger et al. |
| 5,498,338 A | 3/1996 | Kruger et al. |
| 5,725,777 A | 3/1998 | Taylor |
| 5,951,863 A | 9/1999 | Kruger et al. |
| 6,274,103 B1 | 8/2001 | Taylor |
| 6,394,992 B1 | 5/2002 | Sjoeholm |
| 6,572,255 B2 * | 6/2003 | Husher ............... 366/132 |
| 6,719,745 B1 | 4/2004 | Taylor |
| 6,745,903 B2 | 6/2004 | Grandics |
| 6,814,724 B2 | 11/2004 | Taylor |
| 6,905,604 B2 | 6/2005 | Taber |
| 6,908,546 B2 | 6/2005 | Smith |
| 6,977,047 B2 | 12/2005 | Nunez |
| 7,072,742 B1 * | 7/2006 | Bellafiore et al. ............. 700/265 |
| 7,122,149 B2 | 10/2006 | Li et al. |
| 2002/0134736 A1 | 9/2002 | Burris et al. |
| 2003/0094406 A1 | 5/2003 | Smith |
| 2003/0173297 A1 | 9/2003 | Grandics |
| 2004/0079700 A1 | 4/2004 | Wood et al. |
| 2004/0109788 A1 | 6/2004 | Li et al. |
| 2005/0056594 A1 | 3/2005 | Nunez |
| 2005/0121388 A1 | 6/2005 | Wood et al. |
| 2005/0171501 A1 | 8/2005 | Kelly |

* cited by examiner

TOTAL FLUID MANAGEMENT SYSTEM

CROSS REFERENCE TO RELATED APPLICATION

This application claims the benefit of U.S. Provisional Application No. 61/401,884, filed Aug. 20, 2010, the disclosure of which is hereby incorporated by reference in its entirety.

FIELD OF THE INVENTION

The present invention generally relates to fluid management systems, and more particularly to systems for management of injectable fluids for medical procedures.

BACKGROUND OF THE INVENTION

For years, medical practitioners have used injectable fluids during medical procedures. The most common of these injectable fluids is often referred to as "saline solution", or just "saline" which is a sterile aqueous solution of approximately 0.9% weight per volume solution of sodium chloride (NaCl). Saline solution is typically used for intravenous infusion, but may also be used externally for certain irrigation techniques and other medical procedures and techniques. Saline solution is also often combined with other substances, usually medications, prior to injection.

Commonly, saline solution is transported in, and used out of, plastic bags which are typically each one liter or three liter in volume. These bags are made of plastic, most commonly polyvinyl chloride (PVC), and are considered to be disposable.

The use of one- and three-liter bags causes a multitude of problems. First, the bags, including the sterile saline solution must be continually delivered to the hospital or other medical facility. Second, after use, the bags being disposable creates unneeded waste. Third, if a full bag is not used during a procedure, a portion of unused saline solution will likely go to waste and have to be disposed of. Fourth, many medical procedures require the use of multiple bags, thus requiring additional labor for opening and switching bags during procedures.

The system of the present invention preferably includes a stationary water purification station connected to a water feed. The stationary water purification station includes a plurality of components for purifying and storing water for use in medical procedures. The system also preferably includes a portable fluid station that is attachable aseptically to the stationary water purification station. The portable fluid station also includes a plurality of components including concentrated saline in liquid or powder form, and a large tank or bag for storage of an amount of saline solution to be used in one or medical procedures.

A method of providing an injectable fluid such as saline solution is also part of the present invention. The method generally includes providing a stationary water purification docking station including at least one filter and providing a portable fluid station which is movable toward and away from and dockable to the water purification station. The portable fluid station preferably comprises a concentrate source containing a water soluble concentrate therein, a mixer to mix purified water with a concentrated solution, and a fluid receptacle for receiving and retaining fluid therein. Additionally, water is conveyed through the filter, the portable fluid station is docked to the stationary water purification station, the purified water is conveyed from the stationary water purification station to the portable fluid station, the purified water is mixed with the water soluble concentrate, the injectable-grade fluid is retained in a fluid receptacle, and at least a portion of the injectable-grade fluid is removed from the portable fluid station for use in a medical procedure. Such uses include, but are not limited to, irrigation, joint distension procedures, and distension of body cavities.

Other objects and purposes of the invention, and variations thereof, will be apparent upon reading the following specification and inspecting the accompanying drawings.

Figure 1:
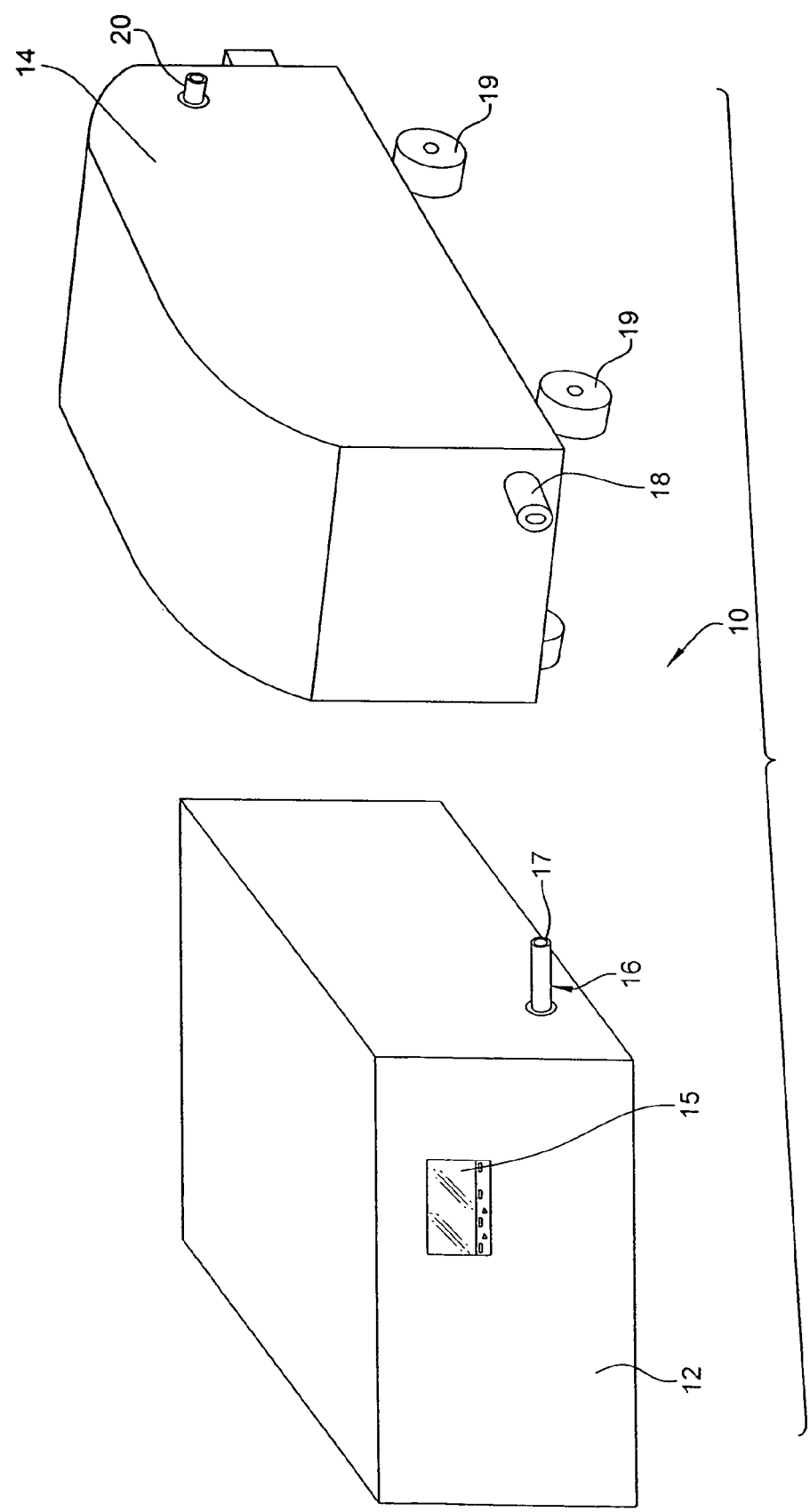
FIG. 1 is a perspective view of a water purification station and a portable fluid station of the present invention.

Certain terminology will be used in the following description for convenience and reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. Said terminology will include the words specifically mentioned, derivatives thereof, and words of similar import.

DETAILED DESCRIPTION OF THE PREFERRED EMBODIMENT

Figure 2:
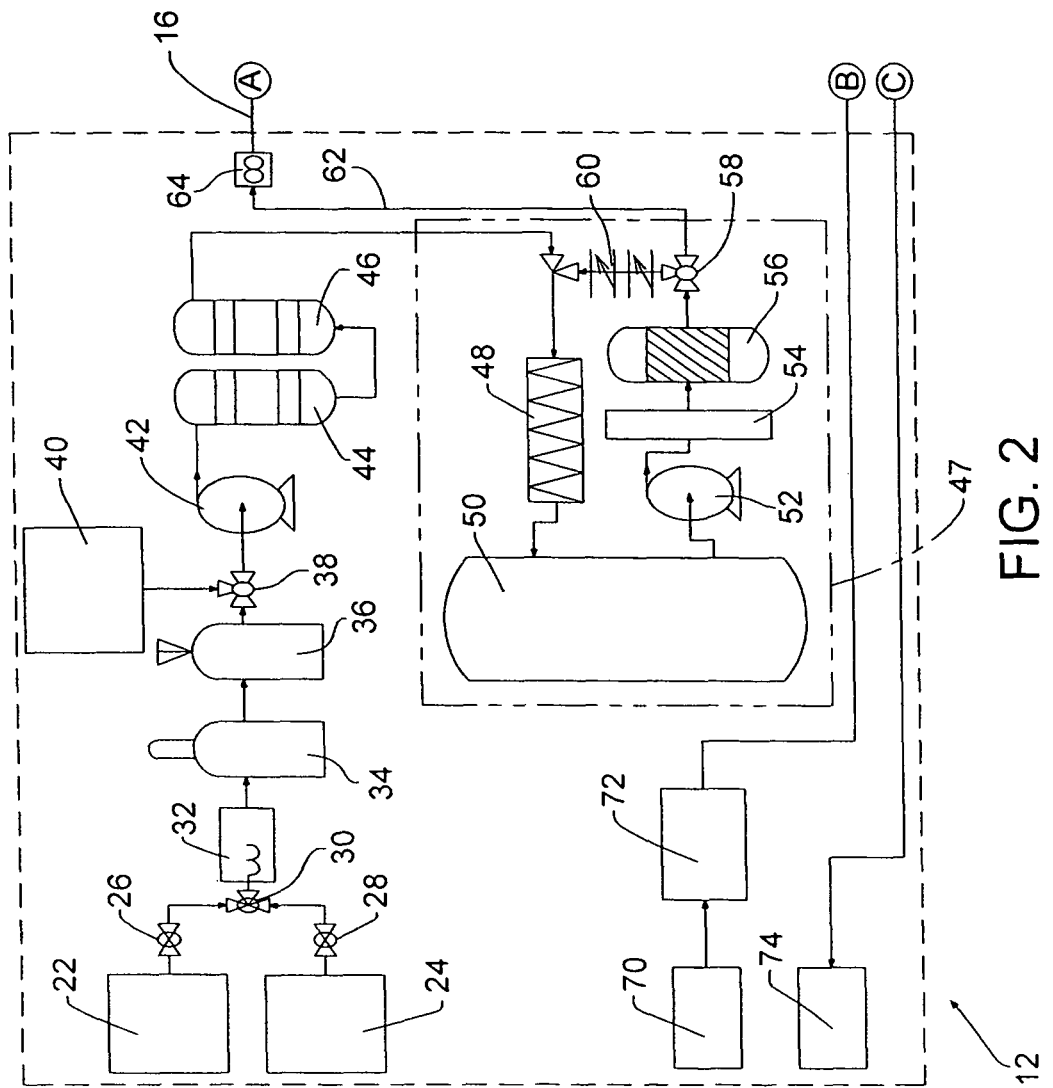
FIG. 2 is a schematic of the interior of the water purification station of FIG. 1.
Figure 3:
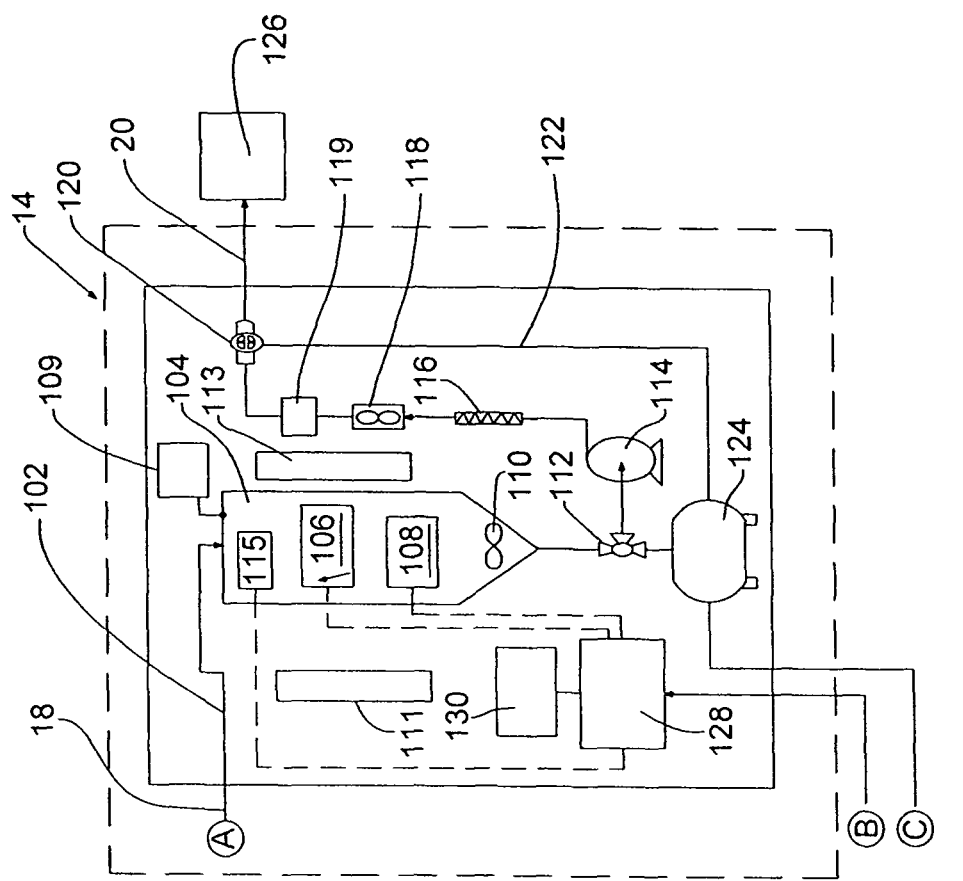
FIG. 3 is a schematic of the interior of the portable fluid station of FIG. 1.

A preferred embodiment of a fluid management system 10 is shown in FIGS. 1-3. The fluid management system generally includes a stationary water purification station 12 and a portable fluid station 14 which is dockable to the stationary water purification station 12, as discussed in more detail below.

The exterior of the water purification station 12 includes an electronic input device 15 which includes a display and a variety of input buttons to control such things as the volume of purified water to be dispensed to the portable fluid station 14 at a given time. The water purification station 12 also includes an output port 16 which is connectable to a docking port of the portable fluid station 14. The outlet port 16 includes a pipe 17, which is configured for an aseptic connection to the portable fluid station 14 so that purified water may be delivered without contamination.

The portable fluid station 14 includes on its exterior a docking port 18 which is configured for aseptic connection to the outlet port 16 of the water purification station 12. The aseptic connection, as referred to above, allows transfer of purified water from the water purification station 12 to the portable fluid station 14 without contamination. The portable fluid station 14 also includes wheels 19 or other transporting means such as castors so that the portable fluid station may be moved to a variety of locations depending on whether it is being filled with purified water or whether it is in use at one or more medical procedure locations. A sterile port 20, which provides an aseptic connection, is also included for administration of saline solution that is dispensed from the portable fluid station 14.

The interior of the water purification station 12 includes a multitude of components, as shown schematically in FIG. 2. A hot water feed 22 and a cold water feed 24 are included to provide a source of non-purified water. The arrows moving away from the water feeds 22, 24 show the general direction of water through the water purification station, to and through the various components discussed in more detail below.

Valve 26 and valve 28 are located downstream of hot water feed 22 and cold water feed 24, respectively, to allow restriction or prevention of water flow from either the hot water feed 22 or cold water feed 24, or both. A three-way valve 30 combines the hot water stream and the cold water stream. Located downstream of the three-way valve 30 is a temperature controller 32. The temperature controller 32 ensures that the water temperature leaving the temperature controller is at a set, substantially homogenous temperature. The preferred water temperature for this system is 25° C., but may be any desired temperature that is suitable. A carbon filter 34 is immediately downstream of temperature controller 32.

Adjacent the carbon filter 34 resides a pre-filter 36. Immediately downstream of the pre-filter 36 is a disinfection valve 38 that is in fluid communication with a cleaner/disinfectant source 40. Examples of such cleaners and disinfectants include one or more of chemical cleaners and disinfectants, ozone, UV and heat. The cleaner, disinfectant, and associated valve 38 ensure that the water is disinfected before being pumped through the reverse osmosis filters described below.

A pump 42 is located downstream from the disinfection valve 38 and is in fluid communication with two reverse osmosis filters 44, 46 which are in series. Adjacent the reverse osmosis filters 44, 46 is a storage and delivery system 47. The storage and delivery system 47 includes a heater 48 for heating the purified water prior to the purified water entering a storage tank 50. The storage tank should be equipped to store purified water and preferably holds a substantial amount of water, such as 50 liters. However, it is contemplated that any reasonable size storage tank or container could be used depending on the space limitations and quantity of use of saline solution at the particular medical facility or location.

In fluid communication with and downstream from the storage tank 50 is a delivery pump 52, which is capable of pumping purified water through a filter, such as an ultrafilter 56, and into an attached portable fluid station. Immediately downstream of the delivery pump 52 is an ultraviolet light 54 for endotoxin destruction. Ultrafilter 56, which is a filter with a dense membrane to prevent the passage of suspended particles, is located adjacent the UV light, and feeds into a second three-way valve 58. The three-way valve 58 allows the purified water to either be discharged through a line 62 and through the outlet port 16 or to be returned through the heater 48 and into the storage tank 50. The return includes at least one back flow prevention valve 60 so that purified water intended to be returned to the tank 50 does not escape to the line 62 for discharge through outlet port 16. Adjacent outlet port 16 is a flow meter 64 for determining the flow rate, either by volume or mass, of purified water flowing through outlet port 16.

The water purification station 12 also includes a power source 70 which is capable of powering various electrical components 72 of the water purification station, as well as electrical components 128 of the fluid station 14 (see FIG. 3) when the portable fluid station 14 is docked to the water purification station 12. The water purification station 12 additionally preferably includes a waste receptacle 74 for receiving waste liquid from the portable fluid station 14 when the portable fluid station 14 is docked to the stationary water purification station 12.

Referring to FIG. 3, attached to the docking port 18 is an inlet pipe 102 that is in fluid communication with a storage tank or bag 104. The storage bag/tank 104 is preferably bigger than 3 liters in volume and more preferably about 30 liters. The storage bag/tank 104 preferably includes a conductivity sensor 106 to ensure that the saline solution is consistently the desired concentration of NaCl, typically 0.9% weight per volume. It is contemplated that other solutions, or concentrations of NaCL, may be used. Such other solutions include 0.9% NaCl with dextrose, 0.45% NaCl, 0.45% NaCl with dextrose, sterile water, and Lactated Ringer's solution. The storage bag/tank 104 also preferably includes a volume meter 108 to determine the volume of saline solution in the storage bag 104. The data received by the volume meter 108 may be used internally electronically such as for an automatic electronic shut-off or may be used externally by the user to determine whether more saline solution needs to be added to the storage bag 104.

The portable fluid station 14 also includes a saline concentrate source 109. The concentrate source 109 may contain either powder or liquid NaCl concentrate, which may be delivered to the storage bag or tank 104 in the appropriate ratio with purified water entering the storage bag/tank 104 via the input line 102. To ensure a homogenous mixture, the portable fluid station 14 also includes a vibration or circulation device for mixing the purified water with the concentrated NaCl. Preferably, an impeller 110 resides in the storage bag/tank 104 and is used to thoroughly mix the saline solution. Such impeller 110 may be electrical in nature, connected directly to a drive shaft, or magnetically coupled to a driver. Two ultraviolet lights 111, 113 are located adjacent the storage bag/tank 104 for decontamination of the saline solution. A sterility validation device 115 may also be used to determine the age of the fluid in the storage bag/tank 104 and compare that age to a predetermined age to ensure that the age and sterility is at an acceptable level for a medical procedure.

Downstream of the storage bag/tank 104 a three-way valve 112 is employed, with outputs to a pump 114 and a waste storage tank 124. The pump 114 may be any sort of pump that is reasonably sized and sufficient to pump the needed amount of saline solution out of the portable fluid station 14, through a cannula and trocar to a patient.

Downstream from pump 114 resides a heater 116 for heating the saline solution to a desired temperature before it reaches the user and/or patient. A flow meter 118 and pressure sensor 119 are also included to insure proper volume, pressure, and flow rate of saline solution out of the portable fluid station 14, and a waste valve 120 is included such that premature shut-off or any overflow may be purged from the system. In such case, the amount of saline solution which does not discharge out of the outlet port 16 is pumped through a waste line 122, which is attached to the waste valve 120, so that the extra saline solution is conveyed to the waste storage tank 124. Saline solution accumulated in the waste storage tank 124 is removed from the waste storage tank 124 upon docking of the portable fluid station 14 to the water purification station 12. Upon docking and initiating waste removal, the saline solution residing in the waste storage tank is discharged to the waste receptacle 74 of the water purification station 12 for later disposal. Saline solution that is intended for use exits through port 20 and to the end user or patient 126.

The portable fluid station 14 also includes electrical components 128 which are connected electrically to the electrical components 72 of the water purification station 12 when station 14 is connected to station 12, and thus to the power supply 70. A battery 130 or other self-contained power source is also provided in the portable fluid station 14 to provide power to the electrical components 128 such that the electrical components 128 may be used when the portable fluid station 14 is not docked to the water purification station 12.

In operation, one or both valves 26, 28 are open to allow water from one or both of the hot water feed 22 and the cold water feed 24 to enter the system. The water streams mix at the three-way valve 30, and the resultant water stream flows through the temperature controller 32 to ensure that the temperature of the water stream 13 is at a desired temperature such as 25° C. The water then flows through the carbon filter 34, into and through pre-filter 36, and then reaches the disinfection valve 38 where the water is disinfected.

The disinfected water is then transported by pump 42 into the first reverse osmosis filter 44 and then into and through the second reverse osmosis filter 46, and then flows through the heater 48 and into the storage tank 50. The filtered water sits in the storage tank 50 until a portable fluid station 14 is docked to the water purification station 12, and a user inputs the appropriate data into the controller 15 indicating that the user desires the given portable fluid station 14 be replenished with purified water.

Upon the user entering the correct input data into the controller 15, delivery pump 52 is activated which pumps filtered water from storage tank 50 past the UV light 54, through the ultrafilter 56, and through the three-way valve 58. If the purified water is not returned through the heater 48 and again into the storage tank 50, due to valve safety and/or quality settings, it flows through discharge line 62, past flow meter 64 and ultimately reaches the outlet port 16. Due to the aseptic connection between outlet port 16 and docking port 18, the purified water flows through the outlet pipe 17 and into the portable fluid station 14 without being contaminated.

Upon reaching the portable fluid station 14, the purified water flows through the input line 102 and into the storage bag/tank 104. At the same time that the purified water is entering the storage bag/tank 104, the station 14 automatically discharges an amount of NaCl from the concentrate source 109 into the storage bag/tank 104 to effectively create the desired concentration of saline solution, which is typically 0.9% by weight. The impeller 110 is then activated to effectively stir and mix the solution, to create a substantially homogeneous solution. The two UV lights 111, 113 are activated to ensure decontamination of the saline solution.

After the saline solution is prepared to a substantially homogenous solution and exposed to the UV light, if a user wishes to discharge saline solution from the portable fluid station 14, a manual or electronic switch is activated to open three-way valve 112. Simultaneously, pump 114 is activated to drive the desired amount of saline solution through the heater 116, past the flow meter 118, and through the waste valve 120. The saline solution to be used exits through sterile port 20 to an end user or patient 126, for such uses as irrigation or distension of joints of body cavities.

If there is unused saline solution remaining in the lines of the portable fluid station 14, such saline solution may be transported to the waste storage tank 124 directly from three-way valve 112 or from the waste valve 120 via the waste line 122, and upon docking pumped into waste receptacle 74.

The system and method of the present invention provide significant advantages over the use of saline plastic bags that are currently in use. The system of the present invention produces usable saline solution at the point of use and allows portability within the medical facility. The cost savings and waste savings that this system provides are significant over the currently used one-liter or three-liter saline plastic disposable bags. Moreover, the system of the present invention significantly decreases saline waste, resulting in less water usage and less waste disposal cost.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method of dispensing an injectable fluid during a medical procedure, the method comprising the steps of:
   (a) providing a water purification docking station comprising at least one filter and a purified water outlet downstream of and in fluid communication with the at least one filter;
   (b) providing a portable fluid station which is moveable toward and away from and dockable to the water purification docking station, the portable fluid station comprising:
   a concentrate source containing a water-soluble concentrate therein,
   a mixer adapted to mix purified water with the water-soluble concentrate, and
   a fluid receptacle disposed to receive and retain a fluid therein;
   (c) conveying water through the at least one filter of the water purification docking station to create purified water;
   (d) moving the portable fluid station adjacent the water purification docking station;
   (e) docking the portable fluid station to the water purification docking station;
   (f) conveying the purified water from the purified water outlet of the water purification docking station to the portable fluid station;
   (g) mixing the purified water with the water-soluble concentrate by activating the mixer of the portable fluid station to create an injectable fluid;
   (h) retaining the injectable fluid in the fluid receptacle; and
   (i) removing at least a portion of the injectable fluid from the fluid receptacle and transporting injectable fluid away from the portable fluid station for use in a medical procedure.

2. The method of claim 1, wherein the fluid receptacle has a volume greater than 3 liters.

3. The method of claim 1, wherein the injectable fluid is a saline solution.

4. The method of claim 1, and further comprising the step of monitoring the injectable fluid to ensure that the sterility and quality of the injectable fluid is acceptable pursuant to given medical standards.

5. The method of claim 1, and further comprising the step of disinfecting the fluid receptacle and its contents with a disinfectant prior to the step of removing at least a portion of the injectable fluid from the fluid receptacle and away from the portable fluid station.

6. The method of claim 1, wherein the step of removing at least a portion of the injectable fluid from the fluid receptacle and away from the portable fluid station occurs at a first location, the method further comprising, after the step of removing at least a portion of the injectable fluid from the fluid receptacle and away from the portable fluid station, the steps of:
   (a) moving the portable fluid station to a second location; and
   (b) pumping at least a portion of the remaining injectable fluid out of the fluid receptacle and away from the portable fluid station.

7. The method of claim 1, and further comprising the step of undocking the portable fluid station from the water purification docking station prior to the step of removing at least a portion of the injectable fluid from the fluid receptacle and away from the portable fluid station.

8. The method of claim 7, and further comprising the step of moving the portable fluid station to a location not adjacent the water purification docking station prior to the step of removing at least a portion of the injectable fluid from the fluid receptacle and away from the portable fluid station.

9. The method of claim 1, further including locating the mixer within the fluid receptacle.

10. The method of claim 9, wherein the mixer is an impeller and further including rotating the impeller within the fluid receptacle.

11. The method of claim 1, further including providing the water purification docking station with a first UV light source, providing the portable fluid station with a second UV light source, moving the purified water past the first UV light source and moving the injectable fluid past the second UV light source.

12. The method of claim 1, further including powering a pump in the portable fluid station with a power source in the water purification docking station.

13. A system for dispensing an injectable fluid during a medical procedure comprising:
- a water purification docking station comprising at least one filter and a purified water outlet downstream of and in fluid communication with the at least one filter;
- a portable fluid station which is moveable toward and away from and dockable to the water purification docking station;
- the portable fluid station comprising a concentrate source containing a water-soluble concentrate therein, a mixer adapted to mix purified water with the water-soluble concentrate, and a fluid receptacle disposed to receive and retain a fluid therein;
- the water purification docking station creating purified water by conveying water through the at least one filter thereof;
- the portable fluid station being adapted to be moved adjacent the water purification docking station;
- the portable fluid station being adapted to be docked to the water purification docking station;
- the water purification docking station being adapted to convey the purified water from the purified water outlet thereof to the portable fluid station;
- the purified water being mixed with the water-soluble concentrate by activating the mixer of the portable fluid station to create an injectable fluid;
- the injectable fluid being retained in the fluid receptacle;
- wherein at least a portion of the injectable fluid is configured to be removed from the fluid receptacle and transported away from the portable fluid station for use in a medical procedure.

* * * * *